(12) United States Patent
Coca et al.

(10) Patent No.: US 7,473,805 B2
(45) Date of Patent: Jan. 6, 2009

(54) PROCESS FOR OBTAINING TOLTERODINE

(75) Inventors: Gustavo Pascual Coca, Valladolid (ES); Pablo Martin Pascual, Valladolid (ES); Jorge Martin Juarez, Valladolid (ES)

(73) Assignee: Ragactives, S.L. Parque Tecnologico de Boecillo, Valledolid (ES)

( * ) Notice: Subject to any disclaimer, the term of this patent is extended or adjusted under 35 U.S.C. 154(b) by 0 days.

(21) Appl. No.: 10/583,833

(22) PCT Filed: Dec. 21, 2004

(86) PCT No.: PCT/ES2004/000572

§ 371 (c)(1),
(2), (4) Date: Jun. 11, 2007

(87) PCT Pub. No.: WO2005/061431

PCT Pub. Date: Jul. 7, 2005

(65) Prior Publication Data

US 2007/0254959 A1    Nov. 1, 2007

(30) Foreign Application Priority Data

Dec. 22, 2003    (ES) ................................ 200303032

(51) Int. Cl.
*C07C 209/26*  (2006.01)
*C07C 209/28*  (2006.01)
*C07C 211/03*  (2006.01)
*C07C 47/228*  (2006.01)

(52) U.S. Cl. .................. 564/397; 564/315; 564/398; 568/442

(58) Field of Classification Search .................. None
See application file for complete search history.

(56) References Cited

OTHER PUBLICATIONS

Database CAPLUS on STN, Acc. No. 2003:335062, Richards et al., WO 2003035599 A1 (May 1, 2003) (abstract).*

* cited by examiner

*Primary Examiner*—Brian J Davis
(74) *Attorney, Agent, or Firm*—Mathews, Shepherd, McKay & Bruneau, P.A.

(57) ABSTRACT

The process comprises reacting a compound of formula (II), where R is a hydroxyl protecting group, and the asterisk indicates an asymmetric carbon atom, with diisopropylamine in the presence of a reducing agent; optionally converting the resulting intermediate into a salt and, if so desired, isolating it; removing the hydroxyl protecting group; and if so desired, separating the desired (R) or (S) enantiomer, or the mixture of enantiomers and/or converting the obtained compound into a pharmaceutically acceptable salt thereof. Tolterodine is a muscarinic receptor antagonist useful in treating urinary incontinence and other symptoms of urinary bladder hyperactivity.

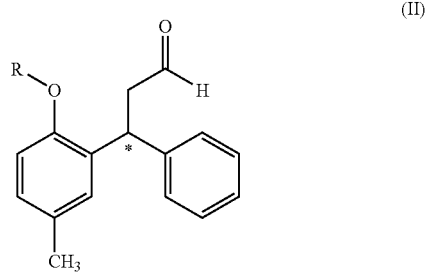

(II)

16 Claims, No Drawings

PROCESS FOR OBTAINING TOLTERODINE

This application is a 371 of PCT/ES04/00572 filed Dec. 21, 2004.

FIELD OF THE INVENTION

The invention relates to a process for obtaining 3-(2-hydroxy-5-methylphenyl)-N,N-diisopropyl-3-phenylpropylamine, its enantiomers or mixtures thereof, or its pharmaceutically acceptable salts, as well as to a new compound useful for the synthesis of said compounds.

BACKGROUND OF THE INVENTION

Tolterodine, the generic name of the compound (R)-3-(2-hydroxy-5-methylphenyl)-N,N-diisopropyl-3-phenylpropylamine, occasionally identified as (R)-tolterodine, is a muscarinic receptor antagonist useful in the treatment of urinary incontinence and other symptoms of urinary bladder hyperactivity. The (S) enantiomer, also known as (S)-tolterodine, and its use in treating urinary and gastrointestinal disorders, has been disclosed in patent document WO 98/03067. U.S. Pat. No. 6,538,035 discloses the use of tolterodine and some of its derivatives in treating asthma in mammals.

Tolterodine was first disclosed in U.S. Pat. No. 5,382,600. Said patent discloses several methods for preparing tolterodine and analogues, generally based on displacing a tosylate with diisopropylamine. Said process has several drawbacks. The displacement reaction occurs very slowly, so several days are required to carry out said reaction, and the total yields are low. Some of the reagents used, such as methyl iodide and lithium and aluminum hydride, are expensive and their use implies a hazard. This makes the overall process more expensive and rather unproductive.

An alternative process for obtaining tolterodine is disclosed in U.S. Pat. No. 5,922,914. Said process comprises reducing 3,4-dihydro-6-methyl-4-phenyl-2H-benzopyran-2-one with DIBAL (diisobutylaluminum hydride) in toluene to give the corresponding hemiketal 6-methyl-4-phenyl-3,4-dihydro-2H-1-benzopyran-2-ol which is then subjected to reductive amination to give racemic tolterodine. This process also has some disadvantages since it uses the reagent DIBAL, which is expensive and hazardous, so carrying out the invention to practice is not suitable at the industrial level.

Patent application WO 03/014060 discloses a process for obtaining tolterodine which, though it partially overcomes some drawbacks of the previous processes, it still includes problematic steps, particularly obtaining the intermediate 3-(2-methoxy-5-methylphenyl)-3-phenylpropanol, its conversion into the tosylate derivative and the subsequent displacement of tosylate with diisopropylamine. These steps still have serious problems, such as the steric hindrance of diisopropylamine in the tosylate displacement reaction, which makes the nucleophilic substitution reaction more difficult, the high temperatures needed for the same, as well as the long reaction times they comprise, even days.

A different approach for preparing the (R)-tolterodine enantiomer consists of several enantioselective syntheses such as those disclosed in U.S. Pat. No. 6,310,248, or by Andersson et al. in J. Org. Chem. 1998, 63, 8067-8070, which disclose processes requiring the participation of asymmetry inducers or chiral auxiliaries, respectively, which are generally very expensive reagents.

It is therefore necessary to solve the problems associated with processes belonging to the state of the art and to provide an alternative process for obtaining tolterodine which improves the cost of the process using more cost-effective and less hazardous reagents and starting materials and which is therefore more productive. Said process must advantageously be susceptible to applying on an industrial scale and must provide the desired product with a good yield and quality.

SUMMARY OF THE INVENTION

The invention is faced with the problem of providing an alternative process for obtaining tolterodine which overcomes all or part of the previously mentioned drawbacks.

The solution provided by the invention is based on the fact that the inventors have observed that it is possible to obtain 3-(2-hydroxy-5-methylphenyl)-N,N-diisopropyl-3-phenylpropylamine, its enantiomers or mixtures thereof, or its pharmaceutically acceptable salts, from a compound of formula (II) (defined below) yielding, by reductive amination with diisopropylamine in the presence of a reducing agent and the subsequent deprotection of the hydroxyl, said compounds in very good yield. In a particular embodiment, the intermediate resulting from reductive amination [compound of formula (III) (defined below)] is converted into a salt, and if so desired said salt is isolated before removing the hydroxy protecting group. Said compound of formula (II) can be obtained from commercial, cost-effective starting compounds.

A process such as the one provided by this invention has the advantage that the chemical reactions involved occur with high yields, with short reaction times, typically less than those required in other processes in the state of the art, without involving an increase in the number of synthesis steps with respect to the existing processes. Furthermore, if the compound of formula (III) is isolated in the form of a salt, for example hydrobromide, before removing the hydroxyl protecting group, a substantially pure product is obtained constituting the starting material to obtain, by means of hydrolysis of the hydroxyl protecting group, 3-(2-hydroxy-5-methylphenyl)-N,N-diisopropyl-3-phenylpropylamine, its enantiomers or mixtures thereof, or its pharmaceutically acceptable salts, with a high purity and yield. Nor does said process require the use of expensive and/or hazardous reagents and provides 3-(2-hydroxy-5-methylphenyl)-N,N-diisopropyl-3-phenylpropylamine, its enantiomers or mixtures thereof, or its pharmaceutically acceptable salts, particularly (R)-tolterodine, with good yield and pharmaceutical quality. This all contributes to reducing the overall cost of the process, making it commercially interesting and allowing carrying it out to practice on an industrial level.

Therefore one aspect of the invention consists in a process for obtaining 3-(2-hydroxy-5-methylphenyl)-N,N-diisopropyl-3-phenylpropylamine, from a compound of formula (II). Resolution of the compound 3-(2-hydroxy-5-methyl-phenyl)-N,N-diisopropyl-3-phenylpropylamine at its (R) enantiomer yields therapeutically useful (R)-tolterodine.

An additional aspect of this invention consists in a compound of formula (II) and its use in obtaining 3-(2-hydroxy-5-methylphenyl)-N,N-diisopropyl-3-phenylpropylamine, its enantiomers (R) and (S) or mixtures thereof, or its pharmaceutically acceptable salts.

Another additional aspect of this invention consists in a process for obtaining said compound of formula (II).

Another additional aspect of this invention consists in a salt of a compound of formula (III) and its use in obtaining 3-(2-hydroxy-5-methylphenyl)-N,N-diisopropyl-3-phenylpropylamine, its enantiomers (R) and (S) or mixtures thereof, or its pharmaceutically acceptable salts. In a particular embodiment, said salt is an inorganic acid addition salt, such as hydrobromide.

Another additional aspect of this invention consists in a process for obtaining said salt of the compound of formula (III).

DETAILED DESCRIPTION OF THE INVENTION

In one aspect, the invention provides a process for obtaining 3-(2-hydroxy-5-methylphenyl)-N,N-diisopropyl-3-phenylpropylamine of formula (I)

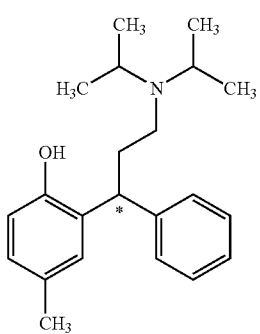

(I)

wherein the asterisk indicates an asymmetrical carbon atom;

its enantiomers or mixtures thereof, or its pharmaceutically acceptable salts, comprising:

(a) reacting compound of formula (II)

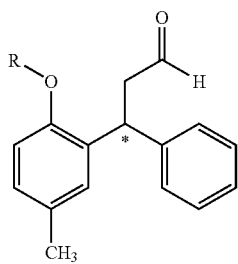

(II)

wherein R is a hydroxyl protecting group and the asterisk has the previously indicated meaning;

with diisopropylamine in the presence of a reducing agent to give a compound of formula (III)

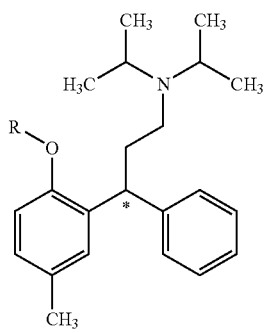

(III)

wherein (R) and the asterisk have the previously indicated meanings;

(b) removing the hydroxyl protecting group from the compound of formula (III) to obtain the compound of formula (I); and (c) if so desired, separating the desired (R) or (S) enantiomer, or the mixture of enantiomers, and/or converting the compound of formula (I) into a pharmaceutically acceptable salt thereof.

In a particular embodiment, the intermediate of formula (III) is converted into a salt, and if so desired is isolated before removing the hydroxyl protecting group [step (b)].

The starting product, compound of formula (II), is a new compound that can be obtained by means of a process such as the one described below.

As it is used in this description, the term "hydroxyl protecting group" includes any group capable of protecting a hydroxyl group. Examples of hydroxyl group protecting groups have been disclosed by Green T W et al. in "Protective groups in Organic Synthesis", $3^{rd}$ Edition (1999), Ed. John Wiley & Sons (ISBN 0-471-16019-9). Though virtually any hydroxyl protecting group can be used, in a particular embodiment the hydroxyl protecting group is a $C_1$-$C_4$ alkyl group, an optionally substituted benzyl group, aralkyl, silyl ether, carbonate or benzyl ester. The term "$C_1$-$C_4$ alkyl" refers to a radical derivative of a linear or branched alkane with 1 to 4 carbon atoms, for example, methyl, ethyl, n-propyl, isopropyl, n-butyl, t-butyl, etc. In a particular embodiment, the hydroxyl protecting group is a $C_1$-$C_4$ alkyl group, preferably methyl or a benzyl group.

The reaction of the compounds of formula (II) with diisopropylamine in the presence of a reducing agent constitutes a reductive amination. Though virtually any suitable reducing agent can be used in said reaction, in a particular embodiment when R is methyl, the reducing agent is selected from NaBCNH$_3$ and NaB(AcO)$_3$H, preferably NaB(AcO)$_3$H, or alternatively, the reduction is carried out by means of hydrogenation in the presence of the suitable catalyst, for example an optionally supported metal catalyst, such as Pd/C, etc. This reaction is carried out in an organic solvent, such as an ether, for example tetrahydrofuran (THF), etc., a halogenated hydrocarbon, for example, dichloromethane, etc., an alcohol, for example, methanol, etc., acetonitrile, etc. Reductive amination occurs through the corresponding "immonium salt" intermediate and can be carried out either in two consecutive steps, ammonium salt formation and subsequent reduction, or in a single step (one-pot), both alternatives falling within the scope of this invention. Reductive amination occurs with a high yield, typically exceeding 90%, thus contributing to the high overall yield of the process of obtaining the compound of formula (I) provided by this invention. In a particular embodiment, when R in the compound of formula (II) is methyl, this reductive amination step is carried out at a temperature comprised between −20° C. and 40° C., preferably between 0° C. and 20° C.

The removal of the hydroxyl protecting group from the compound of formula (III) to obtain the compound of formula (I) can be carried out by conventional methods, for example by means of treating with mineral acids, Lewis acids, organic sulfides, etc. In a particular embodiment, when R in the compound of formula (III) is methyl, the removal of the hydroxyl protecting group is carried out by treating with aqueous hydrobromic acid in acetic acid, and optionally in the presence of a phase transfer catalyst, such as an alkylammonium halide, for example tetrabutylammonium bromide. This step is carried out at the suitable temperature, depending on the species involved, which may easily be determined by a person skilled in the art; in a particular embodiment, when R in the compound of formula (III) is methyl, the removal of said hydroxyl protecting group is carried out at a temperature comprised between 90° C. and 150° C., preferably between 110° C. and 120° C.

Alternatively, the intermediate of formula (III) can be converted into a salt which, if so desired, can be isolated before removing the hydroxyl protecting group [step (b)]. To that purpose, said compound of formula (III) is reacted with a suitable acid in a suitable solvent, such as an ester, an alcohol, etc., thereby forming the corresponding acid addition salt due to the presence of the amino group in said intermediate. Virtually any organic or inorganic acid can be used to form said salt of the compound of formula (III). In a particular embodiment, said acid is an inorganic acid. Illustrative non-limiting examples of said salts of the compound of formula (III) include hydrochloride, hydrobromide, sulfate, etc. Said salt will advantageously be a salt that can be isolated from the reaction medium, for example hydrobromide. The compound of formula (I) can be obtained from the salt of the compound of formula (III) by removal of the hydroxyl protecting group, which may be carried out by any of the previously mentioned methods in relation to the removal of the carboxyl protecting group in the compounds of formula (III). Advantageously, when the anion of the salt of the intermediate of formula (III) is a pharmaceutically acceptable anion, the product resulting from the removal of the hydroxyl protecting group may be a pharmaceutically acceptable salt of the compound of formula (I). Said product may be obtained with a high purity, which simplifies its purification to a pharmaceutical quality grade. Therefore, the isolation of the salt from the compound of formula (III) contributes to the purification of the intermediate of formula (III) since the impurities would remain in the reaction mother liquor, and accordingly, upon converting said intermediate into the compound of formula (I), a final product substantially free of impurities which virtually does not need subsequent purifications is obtained.

In a particular embodiment, the salt of the compound of formula (III) is N,N-diisopropyl-3-(2-methoxy-5-methylphenyl)-3-phenylpropylamine hydrobromide. Said acid addition salt can be obtained by reacting the compound of formula (III) with hydrobromic acid and acetic acid in a suitable organic solvent, such as ethyl acetate, isopropanol, isobutanol, etc. and maintaining the pH between 3 and 5, thereby precipitating said salt, which facilitates its isolation (Example 8). A substantially pure, i.e. virtually free of impurities, and stable solid is thus obtained, which may constitute the starting material for obtaining the compound of formula (I), its enantiomers or mixtures thereof, or its pharmaceutically acceptable salts, for example, hydrobromide, after removal of the hydroxyl protecting group. Using said N,N-diisopropyl-3-(2-methoxy-5-methylphenyl)-3-phenylpropylamine hydrobromide salt, the removal of the hydroxyl protecting group by means of hydrolysis with hydrobromic and acetic acid occurs at short reaction times (typically in 4-6 hours compared to 2-3 days used in other processes), obtaining as a resulting product the hydrobromide of the compound of formula (I), a pharmaceutically acceptable salt, with a high purity, typically with a purity exceeding 99.5%, thus being just a simple purification necessary, for example with methanol, to obtain a final product with a purity of 99.8% or more.

The compound of formula (I) is an amine and can form addition salts with organic or inorganic acids when it reacts with the suitable acids. Examples of said salts include hydrochloride, hydrobromide, sulfate, methanesulfonate, phosphate, nitrate, benzoate, citrate, tartrate, fumarate, maleate, (WO 98/29402). Said salts can be obtained by conventional methods by reacting the free amine with the mentioned acid. In a particular embodiment, said salt is a pharmaceutically acceptable salt, for example, hydrobromide. Said salt can be obtained either by reacting the free amine with hydrobromic acid or as a result of conducting removal of the hydroxyl protecting group by treating with hydrobromic acid. If so desired, said addition salt can optionally be converted into the corresponding free amine by conventional methods, for example by changing the pH of a solution comprising said salt until the free amine is obtained.

The compound of formula (I) has a chiral carbon. Therefore, the compound of formula (I) exists either in the form of its isolated (R) or (S) enantiomers or in the form of mixtures of said enantiomers. As it is used in this description, the term "mixtures" applied to enantiomers includes both racemic mixtures and mixtures enriched in any one of the enantiomers. The compound of formula (I) can be obtained from a mixture of enantiomers, such as a racemic mixture, of the compound of formula (II) or of the compound of formula (III) or of a salt thereof, or else from the pure enantiomers of said compounds of formula (II) or of formula (III) or of a salt thereof. When the starting material is a mixture of enantiomers, the obtained (R) and (S) enantiomers of the compound of formula (I) can be separated by conventional methods of resolution of mixtures of enantiomers, for example by means of fractional crystallization, conventional chromatographic methods, etc. In a particular embodiment, the compound of formula (I) obtained by means of the process provided by this invention is obtained in the form of a mixture of enantiomers, for example in the form of a racemic mixture. Therefore, if so desired, the obtained mixture of enantiomers can be resolved into its corresponding enantiomers to obtain the desired enantiomer. In a particular embodiment, said enantiomer is the (R) enantiomer [(+)-(R)-3-(2-hydroxy-5-methylphenyl)-N,N-diisopropyl-3-phenylpropylamine] or tolterodine, also known as pharmaceutically useful (R)-tolterodine. In another particular embodiment, said enantiomer is the (S) enantiomer [(−)-(S)-3-(2-hydroxy-5-methylphenyl)-N,N-diisopropyl-3-phenylpropyl-amine] or (S)-tolterodine, which also has therapeutic applications. The resolution of the mixture of enantiomers can be carried out by any conventional method, for example by using chiral chromatographic columns or by means of fractional crystallization of salts of the corresponding enantiomers with the appropriate chiral acids. In a particular embodiment, the separation of the (R) enantiomer from the compound of formula (I) is carried out by means of optical resolution treating the mixture of enantiomers with L-tartaric acid. The (R)-tolterodine salt L-tartrate or any other corresponding salt with a suitable chiral acid, can be recrystallized as many times required to obtain the (R) enantiomer of the compound of formula (I) with the desired purity. If so desired, the obtained enantiomer can also be converted into a pharmaceutically acceptable salt thereof by means of conventional processes known by those skilled in the art.

The starting material, compound of formula (II), can be prepared by oxidation of the corresponding alcohol of formula (IV)

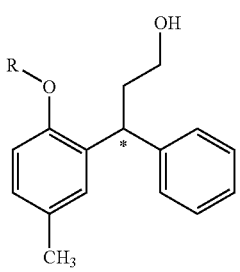

(IV)

wherein R is a hydroxyl protecting group and the asterisk indicates an asymmetric carbon atom.

Oxidation of the alcohol of formula (IV) to obtain the aldehyde of formula (II) can be carried out using any suitable oxidation agent, oxidizing system or method, capable of converting a primary alcohol into the corresponding aldehyde. However, in a particular embodiment, oxidation of the alcohol of formula (IV) into the aldehyde of formula (II) is carried out by using pyridinium chlorochromate (PCC), $SO_3$.pyridine ($SO_3$.pyr), the 2,2,6,6-tetramethylpiperidine (TMPP) N-oxide/NaClO system, or the Swern method, preferably the Swern method [Omura K. & Swern D. Tetrahedron 34:1651 (1978)]. The actuation means required for carrying out said oxidation, for example temperature, solvent, etc., shall be chosen according to the chosen oxidizing agent, system or method.

The alcohol of formula (IV) is a known product, the synthesis of which is disclosed, for example, in patent application WO 03/014060. Said alcohol of formula (IV) may alternatively be obtained by means of a process developed in this invention comprising reacting the compound of formula (V)

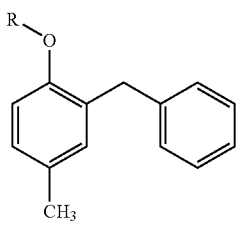

(V)

wherein R is a hydroxyl protecting group;

with ethylene oxide in the presence of a strong base, in a solvent.

Virtually any strong organic or inorganic base capable of withdrawing a proton from the methylene group present in the compound of formula (V) can be used; however in a particular embodiment, said base is an organic or inorganic base such as t-BuOK, BuLi, NaH, $NaNH_2$, MeONa, etc. The reaction is carried out in a suitable solvent, for example dimethylsulfoxide (DMSO), dimethylformamide (DMF) or an ether, such as THF or dioxane, etc. This reaction is carried out at a temperature comprised between −80° C. and +50° C., preferably between −80° C. and −40° C. when the solvent is THF or DMF or between 20° C. and 60° C. when the solvent is DMSO. In a particular embodiment, the deprotonation of the compound of formula (V) is carried out with BuLi in THF, at a temperature comprised between −78° C. and −50° C. and the addition of the oxide ethylene is carried out watching that the temperature does not exceed −50° C.

The compound of formula (V) can be obtained from a compound of formula (VI) by means of a process comprising subjecting said compound to a Friedel-Crafts acylation reaction and subsequent deoxygenation (Alternative A) or to a Friedel-Crafts alkylation reaction (Alternative B). It is possible to prepare the compound of formula (V) by means of any of said alternatives, advantageously in which R is $C_1$-$C_4$ alkyl or benzyl, from simple, accessible and cost-effective starting compounds and reagents, with short reaction times and high yields.

More specifically, obtaining the compound of formula (V) according to Alternative A comprises:

a) subjecting the compound of formula (VI)

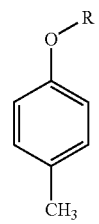

(VI)

wherein R is a hydroxyl protecting group;

to Friedel-Crafts acylation by reaction with a benzoyl halide in the presence of a Lewis acid to give the compound of formula (VII)

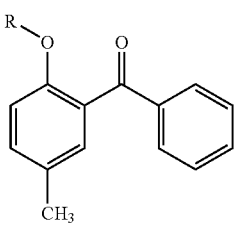

(VII)

wherein R has the previously indicated meaning; and b) subjecting said compound of formula (VII) to a deoxygenation reaction to give the compound of formula (V).

The benzoyl halide can be, for example, benzoyl chloride or benzoyl bromide. Virtually any Lewis acid can be used; however in a particular embodiment, said Lewis acid is tin tetrachloride ($SnCl_4$). Friedel-Crafts acylation is carried out in a suitable solvent, for example dichloromethane, acetonitrile, nitromethane, dioxane, DMF, etc. The addition of the Lewis acid is carried out at a temperature comprised between about 0° C. and 30° C., preferably close to 0° C.

Deoxygenation of the compound of formula (VII) can be carried out by conventional methods, for example by means of the use of a reducing agent suitable for the deoxygenation of ketones. In a particular embodiment, said reducing agent is selected from $NaBH_4$ in the presence of $BF_3$.THF, $NaBH_3CN$ in the presence of $BF_3$.THF, and Zn/HAcO. This reaction is carried out in a suitable solvent, such as an ether, for example, THF, dioxane, etc., a halogenated hydrocarbon, for example dichloromethane, etc., preferably THF.

The deoxygenation reaction can be carried out at a temperature comprised between 20° C. and 100° C., preferably between 50° C. and 70° C.

Obtaining the compound of formula (V) according to Alternative B comprises subjecting said compound of formula (VI) to a Friedel Crafts alkylation by reacting with a benzyl halide in the presence of a Lewis acid to give said compound of formula (V). The benzyl halide can be any suitable benzyl halide, for example benzyl bromide. Virtually any Lewis acid can be used; however in a particular embodiment, said Lewis acid is tin tetrachloride. Friedel-Crafts alkylation is carried out in a suitable solvent, for example acetonitrile, nitromethane, dioxano, DMF, etc. The addition of the Lewis acid is carried out at a temperature comprised between about 0° C. and 30° C., preferably close to 0° C.

In a particular embodiment, the preparation of the compound of formula (V) is carried out according to Alternative A. Although in comparison to Alternative B Alternative A comprises two reaction steps, it has the advantage that the reactions involved occur with high yields (see Example 1) around 78% and 93% respectively, which allows obtaining an intermediate ketone of formula (VII) in a simple manner and with a high yield. Said intermediate ketone can easily be purified by means of conventional recrystallization techniques, whereby a crystalline solid that can be used as a starting material purified in subsequent steps is obtained.

In another aspect the invention relates to the compound of formula (II). In a particular embodiment, the compound of formula (II) is a compound in which R is methyl. The compounds of formula (II) are new compounds, can be used in the synthesis of the compound of formula (I) and therefore constitute an additional aspect of this invention, as does their use in obtaining the compound of formula (I), particularly tolterodine.

In another aspect, the invention relates to a salt of a compound of formula (III), such as an addition salt with an acid. Virtually any organic or inorganic acid can be used to form said addition salt of the compound of formula (III). In a particular embodiment, said acid is an inorganic acid, e.g. hydrochloric acid, hydrobromic acid, sulfuric acid, etc. Non-limiting illustrative examples of said acid addition salts of the compound of formula (III) include hydrochloride, hydrobromide, sulfate, etc. Advantageously, said salt will be a salt that can be isolated from the reaction medium. Also advantageously, the anion of the salt of the compound of formula (III) is an anion of a pharmaceutically acceptable salt, for example, hydrobromide.

In a particular embodiment, said salt of the compound of formula (III) is N,N-diisopropyl-3-(2-methoxy-5-methylphenyl)-3-phenylpropyl-amine hydrobromide.

The salts de the compounds of formula (III) can be obtained by conventional methods by reacting the compound of formula (III) with the organic or inorganic acid at hand in a suitable solvent, such as an ester, an alcohol, etc. Optionally, if so desired said addition salt can be converted into the corresponding free amine [compound of formula (III)] by conventional methods, for example by changing the pH of a solution comprising said salt until the free amine is obtained.

The N,N-diisopropyl-3-(2-methoxy-5-methylphenyl)-3-phenylpropylamine hydrobromide salt can be obtained by reacting the compound N,N-diisopropyl-3-(2-methoxy-5-methylphenyl)-3-phenylpropylamine with hydrobromic acid and acetic acid in a suitable organic solvent, such as ethyl acetate, isopropanol, isobutanol, etc., and by maintaining the pH between 3 and 5, so that said salt precipitates, facilitating its isolation. Said salt constitutes a good starting material for obtaining the compound of formula (I), its enantiomers or mixtures thereof, or its pharmaceutically acceptable salts, for example, hydrobromide, by means of removal of the hydroxyl protecting group.

The salts of the compounds of formula (III) are new compounds, can be used in the synthesis of 3-(2-hydroxy-5-methylphenyl)-N,N-diisopropyl-3-phenylpropylamine, its enantiomers (R) and (S), or mixtures thereof, or its pharmaceutically acceptable salts, and therefore constitute an additional aspect of this invention as does their use in obtaining the compound of formula (I), particularly tolterodine. The process for obtaining said salt of the compound of formula (III) constitutes a further aspect of this invention.

The process provided by this invention allows obtaining the compound of formula (I), its isolated enantiomers or mixtures thereof, and its pharmaceutically acceptable salts, in particular the (R) and (S) enantiomers, from the compound of formula (II). Said compound of formula (II) can be obtained easily and with a good yield from the corresponding alcohol of formula (IV).

The process provided by this invention to obtain the compound of formula (I) has several advantages since it allows, among others, obtaining tolterodine without needing to go through reaction steps having, among other drawbacks, long reaction times; tolterodine can be prepared from simple, cost-effective and accessible starting compounds and reagents that are not expensive and/or hazardous, and it provides tolterodine and/or its pharmaceutically acceptable salts with a good yield and pharmaceutical quality. This all contributes to reducing the overall cost of the process of obtaining tolterodine, making said process commercially interesting and advantageously possible to be carried out to practice at an industrial level.

The following examples illustrate the invention and must not be considered as limiting of the scope thereof.

EXAMPLE 1

2-methoxy-5-methylbenzophenone $SnCl_4$ (47.5 ml, 0.41 mol) was added dropwise to a mixture of 4-methylanisol (100 g, 0.82 mol) and benzoyl (95.15 ml, 0.82 mol) in 500 ml of $CH_2Cl_2$ at 0° C. Once the addition is complete, it was allowed to react for 3-4 hours, allowing the mixture to reach room temperature. Once the reaction concluded, the mixture was cooled at 0° C., hydrolyzed with a mixture of concentrated HCl (41 ml) in $H_2O$ (376 ml), washed with 2×50 ml of NaOH (10%), dried and evaporated to give 140 g (78%) of the title compound in crystalline solid form.

EXAMPLE 2

(2-methoxy-5-methylphenyl)phenylmethane $BF_3$.THF (204 ml, 1.86 mol) and $NaBH_4$ (46.8 g, 1.24 mol) were added to a mixture of 2-methoxy-5-methylbenzophenone (140 g, 0.62 mol), in 840 ml of THF, and it was slowly heated to the reflux temperature (60° C.), maintaining it for about 6 hours. Once the reaction concluded, the mixture was cooled, added to 500 ml of $NaHCO_3$ (7%), and the organic phase was extracted with 200 ml of ethyl acetate, washed with 3×50 ml of $NaHCO_3$ (7%), dried and evaporated, giving a viscous liquid [122.5 g (93%)] containing the title compound.

EXAMPLE 3

3-(2-methoxy-5-methylphenyl)-3-phenylpropanol

BuLi (54.4 ml, 0.147 mol) was added to a solution of (2-methoxy-5-methylphenyl)phenylmethane (24 g, 0.113 mol), in 120 ml of THF at −78° C. Once the addition was complete, it was heated to room temperature and maintained at said temperature for about 2 hours. The temperature was again reduced to −78° C. and ethylene oxide (4.98 g, 0.113 mol) was added such that the temperature did not exceed −50° C. The reaction was allowed to take place, being complete after 2 hours. Then the mixture was hydrolyzed with 60 ml of $NH_4Cl$, extracted with 30 ml of ethyl acetate, the organic phase washed with 2×25 ml of $NH_4Cl$, dried and evaporated, giving 30 g (100%) of a viscous yellow liquid containing the title compound.

EXAMPLE 4

3-(2-methoxy-5-methylphenyl)-3-phenylpropanal

4.1 Oxidation Method (1)

Dimethylsulfoxide (DMSO) (6.72 ml, 94.6 mmol) in 20 ml of $Cl_2CH_2$ was added to a mixture of oxalyl chloride (4.06 ml, 47.3 mmol) in 100 ml of $Cl_2CH_2$ and cooled at −78° C., always maintaining the reaction temperature under −60° C. It was allowed to take place at said temperature for 15 minutes and then a mixture of 3-(2-methoxy-5-methylphenyl)-3-phenylpropanol (9.33 g, 36.4 mmol) in 40 ml of $Cl_2CH_2$ was added. The reaction mixture was maintained for about 45 minutes and triethylamine (25.72 ml, 0.18 mol) was added. The crude reaction product was maintained reacting for about 1 hour and hydrolyzed with 100 ml of $NaHCO_3$ (7%). The extraction was carried out with 100 ml of ethyl acetate. The organic phase washed with 2×25 ml of HCl (5%), dried and evaporated, giving 8.67 g (94%) of a viscous orangish liquid containing the title compound.

4.2 Oxidation Method (2)

3-(2-methoxy-5-methylphenyl)-3-phenylpropanol (0.5 g, 1.95 mmol) dissolved in 1 ml of $Cl_2CH_2$ was added to a suspension of PCC (0.63 g, 2.93 mmol) and 0.5 g of $MgSO_4$ in 4 ml of $Cl_2CH_2$. The reaction was completed after 3 hours. Then it was filtered with celite and the filtrate was extracted with 2×25 ml of HCl (5%). The resulting organic phase was dried and the solvent was evaporated, giving 2.21 g of a dark viscous liquid containing the title compound.

4.3 Oxidation Method (3)

$SO_3.Py$ (1.56 g, 9.75 mmol) was slowly added to a mixture at 0° C. consisting of 3-(2-methoxy-5-methylphenyl)-3-phenylpropanol (0.5 g, 1.95 mmol), 6.5 ml of $Cl_2CH_2$, 0.54 ml of DMSO and triethylamine (2.7 ml, 19.5 mmol). Once the reaction concluded, it washed with a $NH_4Cl$ saturated solution (2×25 ml). The resulting organic phase was dried and the solvent was evaporated, giving 0.45 g of a black viscous liquid containing the title compound.

4.4 Oxidation Method (4)

Metachloroperbenzoic acid (0.04 g, 0.213 mmol) was added to a mixture consisting of 2.5 ml of $Cl_2CH_2$ and 2,2,6,6-tetramethyl-piperidine (TMPP) N-oxide (3 mg, 0.022 mmol) at −10° C., and subsequently 3-(2-methoxy-5-methylphenyl)-3-phenylpropanol (0.5 g, 1.95 mmol) dissolved in 2.5 ml of $Cl_2CH_2$ was added dropwise, maintaining the temperature at −10° C. Then the temperature was increased to 0° C. and a 10% NaOCl solution (1.3 ml, 2.13 mmol) at pH 9.5 was added dropwise, maintaining the reaction for 1 hour. Once this time elapsed, the reaction mixture was treated with water and $Cl_2CH_2$, giving 0.4 g of an impure, dense yellow liquid containing the compound of the title.

EXAMPLE 5

N,N-diisopropyl-3-(2-methoxy-5-methylphenyl)-3-phenylpropylanune 3-(2-methoxy-5-methylphenyl)-3-phenylpropanal (8.67 g, 34.1 mmol) dissolved in 10 ml of THF, as well as diisopropylamine (5.78 ml, 40.92 mmol) were added to a suspension of $NaHB(OAc)_3$ (44.3 mmol) in 70 ml of THF, maintaining the crude reaction product for 2 hours. Once the reaction was concluded, it was hydrolyzed with 25 ml of $NaHCO_3$ (7%), extracted with 25 ml of ethyl acetate, washed with 2×25 ml of HCl (5%), the solvent dried and evaporated, giving 10.52 g (91%) of a viscous yellow liquid containing the title compound.

EXAMPLE 6

N,N-diisopropyl-3-(2-hydroxy-5-methylphenyl)-3-phenylpropylamine Hydrobromide

6.1 Method A

A suspension of N,N-diisopropyl-3-(2-methoxy-5-methylphenyl)-3-phenylpropylamine (10.52 g, 30.99 mmol) in 24 ml of HBr (48%) and 14 ml of acetic acid was heated under reflux (115° C.) for 72 hours. Then, 21 ml of ethyl acetate were added dropwise, it was stirred for 1 hour at 0° C. and filtered, giving 6.5 g (64%) of final product (title compound).

6.2 Method B

A suspension of N,N-diisopropyl-3-(2-methoxy-5-methylphenyl)-3-phenylpropylamine (0.85 g, 2.5 mmol) in 2 ml of HBr (48%), 1.1 ml of acetic acid and 4 mg of tetrabutylammonium bromide (phase transfer catalyst) was heated under reflux (115° C.) for 48 hours. Then, 2 ml of ethyl acetate were added dropwise, stirred for 1 hour at 0° C. and filtered, giving 0.8 g (80%) of final product (title compound).

EXAMPLE 7

R-(+)-N,N-diisopropyl-3-(2-hydroxy-5-methylphenyl)-3-phenylpropylaline Tartrate 5.2 ml of NaOH (50%) were added to a suspension of N,N-diisopropyl-3-(2-hydroxy-5-methylphenyl)-3-phenylpropylamine hydrobromide (53 g, 0.131 mol) in 750 ml of $CH_2Cl_2$ and 375 ml of water, adjusting the pH to 9.5 with acetic acid if necessary. Once this pH was reached, it was maintained under stirring for 45 minutes and extracted with $CH_2Cl_2$, giving 42.55 g of the free amine. Then, a solution of 29.43 g of L-tartaric acid dissolved in 280 ml of ethanol at 60° C. was added to the amine dissolved in 140 ml of ethanol at 60° C. The reaction was maintained at a temperature comprised between 60° C. and 70° C. for 1 hour and cooled slowly to 0° C., maintaining it at said temperature for another hour. The resulting white precipitate was filtered and dried under vacuum for 14 hours, giving 31.08 g of the product.

Then, 1,200 ml of ethanol were mixed with the 31.08 g of product obtained and heated at 80° C. for 30 minutes; the ethanol volume was concentrated to half by distillation and was gradually cooled at room temperature and subsequently for 1 hour at 0° C. Tolterodine L-tartrate was obtained by filtration and it was dried under vacuum at 60° C. for 14 hours, giving 27.51 g of product. This process was repeated a second time with the 27.51 g of recrystallized tolterodine L-tartrate to give 22.23 g with a purity of 99.80% of the optically active compound.

EXAMPLE 8

N,N-diisopropyl-3-(2-methoxy-5-methylphenyl)-3-phenylpropylamine Hydrobromide 3-(2-methoxy-5-methylphenyl)-3-phenylpropanal (8.67 g, 34.1 mmol) dissolved in 10 ml of THF, and diisopropylamine (5.78 mlj 40.92 mmol) were added to a suspension of NaB(AcO)$_3$H (44.3 mmol) in 70 ml pf THF, maintaining the reaction for 2 hours. Once this time elapsed, 25 ml of NaHCO$_3$ (7%) were added, and the resulting product was extracted with 25 ml of ethyl acetate, washed with 2×25 ml of HCl (5%), the solvent was dried and evaporated, giving 10.52 g (91%) of a viscous yellow liquid.

A 33% BrH/CH$_3$—COOH solution was added to the obtained residue redissolved in 40 ml of ethyl acetate and cooled at 10° C. until reaching a pH comprised between 3 and 5 (an aliquot is taken and mixed with water to measure the pH). During the course of the addition, a white solid precipitates which is left under stirring for 1 hour before filtering and washing with more ethyl acetate.

The obtained product is dried to give 7 g of the title product, free of impurities.

Melting point: 179.5-180.5° C.

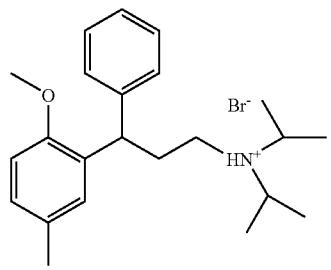

The invention claimed is:

1. A process for obtaining 3-(2-hydroxy-5-methylphenyl)-N,N-diisopropyl-3-phenylpropylamine of formula (I)

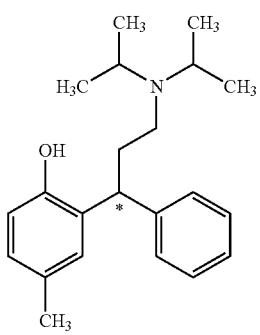

(I)

wherein the asterisk indicates an asymmetric carbon atom, its enantiomers or mixtures thereof, or its pharmaceutically acceptable salts, comprising:

(a) oxidizing the alcohol of formula (IV)

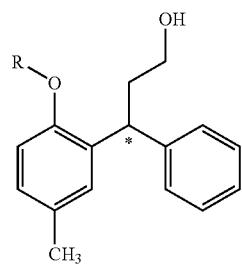

(IV)

wherein the asterisk has the previously indicated meaning and R is a hydroxyl protecting group, to give a compound of formula (II)

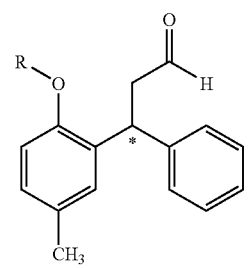

(II)

wherein R and the asterisk have the previously indicated meanings;

(b) reacting the compound of formula (II) with diisopropylamine in the presence of a reducing agent to give a compound of formula (III)

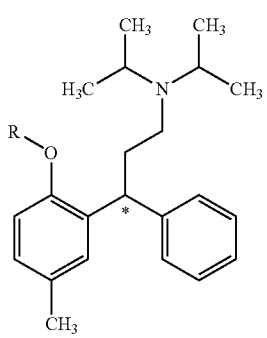

(III)

wherein R and the asterisk have the previously indicated meanings;

(c) removing the hydroxyl protecting group from the compound of formula (III) to obtain the compound of formula (I); and (d) if so desired, separating the desired (R) or (S) enantiomer, or the mixture of enantiomers, and/or converting the compound of formula (I) into a pharmaceutically acceptable salt thereof.

2. A process according to claim 1, wherein said reducing agent is selected from NaBCNH$_3$, NaB(AcO)$_3$H and hydrogen in the presence of Pd/C.

3. A process according to claim 1, wherein the reaction of the compound of formula (II) with diisopropylamine is carried out in a solvent selected from tetrahydrofuran, dichloromethane, acetonitrile and methanol.

4. A process according to claim 1, further comprising converting said compound of formula (III) into a salt, and, if desired, isolating said salt of the compound of formula (III) before removing the hydroxyl protecting group.

5. A process according to claim 4, wherein said salt of the compound of formula (III) is an inorganic acid addition salt.

6. A process according to claim 4, wherein said salt of the compound of formula (III) is N,N-diisopropyl-3-(2-methoxy-5-methylphenyl)-3-phenylpropylamine hydrobromide.

7. A process according to claim 1, wherein the removal of the hydroxyl protecting group from the compound of formula (III), or from said salt of the compound of formula (III), is carried out by means of treating with a mineral acid, a Lewis acid or an organic sulfide.

8. A process according to claim 7, wherein the removal of the hydroxyl protecting group from the compound of formula (III), or from said salt of the compound of formula (III), is carried out by means of treating with aqueous hydrobromic acid in acetic acid.

9. A process according to claim 1, wherein the obtained compound of formula (I) is selected from the (R) enantiomer, the (S) enantiomer and their mixtures.

10. A process according to claim 1, wherein the separation of the (R) or (S) enantiomers from the compound of formula (I) is carried out by means of fractional crystallization of the salts of said enantiomers with chiral acids.

11. A process according to claim 1, wherein the oxidation of the alcohol of formula (IV) to obtain the aldehyde of formula (II) is carried out using pyridinium chlorochromate (PCC), $SO_3$.pyridine ($SO_3$.pyr), the 2,2,6,6-tetramethylpiperidine (TMPP) N-oxide/NaClO system, or the Swern method.

12. A compound of formula (II)

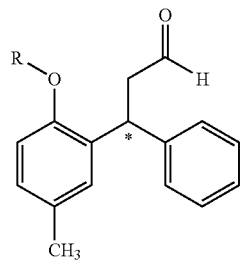

(II)

wherein

R is a $C_1$-$C_4$ alkyl group, an optionally substituted benzyl group, aralkyl, silyl ether, carbonate or benzyl ester; and the asterisk indicates an asymmetric carbon atom.

13. A compound according to claim 12, wherein R is methyl.

14. A process according to claim 5, wherein said salt of the compound of formula (III) is N,N-diisopropyl-3-(2-methoxy-5-methylphenyl)-3-phenylpropylamine hydrobromide.

15. A process according to claim 4, wherein the removal of the hydroxyl protecting group from the compound of formula (III), or from said salt of the compound of formula (III), is carried out by means of treating with a mineral acid, a Lewis acid or an organic sulfide.

16. The process according to claim 5 wherein the salt of the compound of formula (III) is the hydrochloride, hydrobromide or sulfate of the compound of formula (III).

* * * * *